United States Patent [19]
Brandt et al.

[11] Patent Number: 6,106,826
[45] Date of Patent: Aug. 22, 2000

[54] REPLICATION COMPETENT, AVIRULENT HERPES SIMPLEX VIRUS AS A VECTOR FOR NEURAL AND OCULAR GENE THERAPY

[75] Inventors: Curtis R. Brandt, Oregon; Ronald E. Kalil, Madison, both of Wis.; Seema Agarwala, Evanston, Ill.

[73] Assignee: Wisconsin Alumni Research Foundation, Madison, Wis.

[21] Appl. No.: 08/992,250

[22] Filed: Dec. 17, 1997

[51] Int. Cl.[7] .......................... A01N 63/00; A01N 43/04; C12N 15/63

[52] U.S. Cl. ..................... 424/93.2; 514/44; 435/320.1; 435/235.1

[58] Field of Search ............................. 435/320.1, 235.1, 435/325, 455; 424/93.2; 514/44; 536/23.5, 24.1

[56] References Cited

U.S. PATENT DOCUMENTS

| | | | |
|---|---|---|---|
| 5,585,096 | 12/1996 | Martuza et al. | 424/93.2 |
| 5,661,033 | 8/1997 | Ho et al. | 435/320.1 |
| 5,849,571 | 12/1998 | Glorioso et al. | 435/320.1 |

OTHER PUBLICATIONS

Kennedy et al. (Quarterly J. Medicine, (Nov. 1993) 86 (11) 697–702).

Weatherall D. (British Med. Bulletin 1995, vol. 51, No. 1, pp. 1–11).

NIH panel report, Dec. 1995.

M. Ali, et al., "The Use of DNA Viruses As Vectors For Gene Therapy," Gene Therapy, vol. 1 (1994), pp. 367–384.

T. Mineta, et al., "CNS Tumor Therapy by Attenuated Herpes Simplex Viruses," Gene Therapy (Aug. 16–18, 1993), vol. 1, Suppl. 1, p. S78.

E. Boviatsis, et al., "Long–Term Survival of Rats Harboring Brain Neoplasms Treated with Ganciclovir and a Herpes Simplex Virus Vector That Retains an Intact Thymidine Kinase Gene," Cancer Research, vol. 54 (Nov. 15, 1994) pp. 5745–5751.

K. Unoki, et al., "Protection of the Rat Retina From Ischemic Injury by Brain–Derived Neurotrophic Factor, Ciliary Neurotrophic Factor, and Basic Fibroblast Growth Factor," Investigative Ophthalmology & Visual Science, vol. 35, No. 3 (Mar. 1994), pp. 907–915.

M. LaVail, et al., "Basic Fibroblast Growth Factor Protects Photoreceptors from Light–Induced Degeneration in Albino Rats," Annals New York Academy of Sciences, pp. 341–347.

E. Faktorovich, et al., "Photoreceptor Degeneration in Inherited Retinal Dystrophy Delayed by Basic Fibroblast Growth Factor," Nature, vol. 347 (Sep. 6, 1990), pp. 83–86.

S. Andreansky et al., "The Application of Genetically Engineered Herpes Simplex Viruses to the Treatment of Experimental Brain Tumors," Proc. Natl. Acad. Sci. USA, vol. 93 (Oct. 1996), pp. 11313–11318.

C. Kramm, et al., "Herpes Vector–Mediated Delivery of Marker Genes to Disseminated Central Nervous System Tumors," Human Gene Therapy, vol. 7 (Feb. 10, 1996), pp. 291–300.

R. Coffin, et al., "Gene Delivery to the Heart In Vivo and to Cardiac Myocytes and Vascular Smooth Muscle Cells In Vitro Using Herpes Virus Vectors," Gene Therapy, vol. 3 (1996), pp. 560–566.

C. Kramm, "Long–Term Survival in a Rodent Model of Disseminated Brain Tumors by Combined Intrathecal Delivery of Herpes Vectors and Ganciclovir Treatment," Human Gene Therapy, vol. 7 (Oct. 20, 1996), pp. 1989–1994.

J. Sievers, et al., "Fibroblast Growth Factors Promote the Survival of Adult Rat Retinal Ganglion Cells After Transection of The Optic Nerve," Neuroscience Letters, vol. 76 (1987), pp. 157–162.

C. Zhang, et al., "Effects of Basic Fibroblast Growth Factor in Retinal Ischemia," Investigative Ophthalmology & Visual Science, vol. 35, No. 8 (Jul. 1994), pp. 3163–3168.

J. Pepose, et al., "Herpes Simplex Viral Vectors for Therapeutic Gene Delivery to Ocular Tissues," Investigative Ophthalmology & Visual Science, vol. 35, No. 6 (May 1994), pp. 2662–2666.

J. Glorioso, et al., "Development and Application of Herpes Simplex Virus Vectors for Human Gene Therapy," Annu. Rev. Microbiol., vol. 49 (1995), pp. 675–710.

D. Goldstein, et al., "Herpes Simplex Virus Type 1–Induced Ribonucleotide Reductase Activity Is Dispensable for Virus Growth and DNA Synthesis: Isolation and Characterization of an ICP6 IacZ Insertion Mutant," Journal of Virology, vol. 62, No. 1 (Jan 1988), pp. 196–205.

D. Goldstein, "Factor(s) Present in Herpes Simplex Virus Type 1–Infected Cells Can Compensate for the Loss of the Large Subunit of the Viral Ribonucleotide Reductase: Characterization of an ICP6 Delection Mutant," Academic Press, vol. 166 (1988), pp. 41–51.

S. Arab, et al., "The Gene Encoding Bovine Brain–Derived Neurotrophic Factor (BDNF)," Gene, vol. 185 (1997), pp. 95–98.

J. Glorioso, et al., "HSV as a Gene Transfer Vector for the Nervous System," Molecular Biotechnology, vol. 4 (1995), pp. 87–99.

C. Brandt, et al., "The Herpes Simplex Virus Type 1 Ribonucleotide Reductase is Required for Acute Retinal Disease," Arch Virol, vol. 142 (1997), pp. 883–896.

*Primary Examiner*—Deborah J. Clark
*Attorney, Agent, or Firm*—Foley & Lardner

[57] ABSTRACT

Degenerative diseases of the retina are a leading cause of vision loss in the United States, affecting approximately two million people each year. The replacement of a defective gene by gene therapy provides one approach for treating individuals having ocular neuronal degeneration where the defective gene has been identified. Several factors, however, suggest that the replacement of a specific gene in a patient might not be effective. For example, many of the conditions are autosomal dominant, and placing a normal copy of the gene into the cells would not correct the defect. As an alternative, replication competent, avirulent, ribonuclease reductase deficient Herpes simplex virus can provide the means to deliver therapeutic polypeptides in a continuous manner to affected cells. Such therapeutic polypeptides include growth factors, neurotrophins and cytokines.

10 Claims, No Drawings

REPLICATION COMPETENT, AVIRULENT HERPES SIMPLEX VIRUS AS A VECTOR FOR NEURAL AND OCULAR GENE THERAPY

This invention was made with United States government support awarded by the following agencies: National Institutes of Health, Grant Nos: EYO1331; EYO7336. The United States has certain rights in this invention.

BACKGROUND OF THE INVENTION

1. Field of the Invention

The present invention relates to methods for using recombinant Herpes simplex virus to treat neuronal degeneration. More particularly, this invention relates to methods for treating neuronal degeneration, including ocular neuronal degeneration, by administering a Herpes simplex virus that expresses a therapeutic gene in infected cells, but does not express ribonucleotide reductase.

2. Related Art

Degenerative diseases of the retina are a leading cause of vision loss in the United States, affecting approximately two million people each year. VISION RESEARCH—A NATIONAL PLAN, 1994–1988, Report of the National Advisory Eye Council, National Institutes of Health, National Eye Institute, pages 41 and 55; Berson, *Proc. Nat'l Acad. Sci. USA* 93:4526 (1996). Certain retinal degenerations, such as retinitis pigmentosa are clearly inherited and can be classified as autosomal dominant, autosomal recessive, or X-linked. Humphries et al., *Science* 256:804 (1992).

Another major cause of retinal degeneration is macular degeneration. Macular degeneration primarily affects people older than 65 and is a leading cause of blindness in this group. The majority of macular degeneration has not yet been linked to genetic factors and the cause of macular degeneration remains unknown for most patients. VISION RESEARCH—A NATIONAL PLAN, 1994–1988, Report of the National Advisory Eye Council, National Institutes of Health, National Eye Institute, pages 41 and 55.

Recent studies on retinitis pigmentosa have shown that mutations in several genes coding for proteins in the phototransduction pathway are involved. Most are in rhodopsin but the peripherin/rds (retinal degeneration slow) gene, cyclic GMP-phosphodiesterase gene, and the RCC1 guanine nucleotide exchange factor may also be involved. See, for example, Dryja et al., *Proc. Nat'l Acad. Sci. USA*. 88:6481 (1991); Inglehearn et al., *Hum. Mol. Gen.* 1:41–45 (1992); Al-Maghtheh et al., *Hum. Mol. Gen.* 3:205 (1994); Meindl et al., *Nature Genetics* 13:35 (1996). In humans, retinitis pigmentosa has been mapped to other genetic loci indicating that several other genes may be involved in the disease. Humphries et al., *Science* 256:804 (1992). Recent results have also identified a mutation in the human peripherin/rds gene in the cause of autosomal dominant macular dystrophy in three families. McLaughlin et al., *Nature Genetics* 4:130 (1993); Gal et al., *Nature Genetics* 7:64 (1995). These results suggest that both retinitis pigmentosa and macular degeneration may have a common underlying mechanism, defects in phototransduction proteins, and that common strategies for treatment might be possible. Mutations in the rod C-GMP phosphodiesterase β-2 subunit gene have been implicated in autosomal dominant stationary night blindness, again suggesting that defects in phototransduction cascade proteins cause several retinal degenerative diseases. Tsang et al., *Science* 272:1026 (1996).

Gene therapy is certainly one strategy that might be used for treatment in individuals where the defective gene has been identified. Several factors, however, suggest that the replacement of a specific gene in a patient might not be effective. A clinical test to determine the mutation would be required. This is not yet widely available and would likely require that specialized diagnostic centers be established. Moreover, a method for the delivery of the gene to the photoreceptor cells is needed. Finally, many of the conditions are autosomal dominant, and placing a normal copy of the gene into the cells would not correct the defect. Treatment would have to "turn off" the mutant allele, which would be very difficult to do in all cells.

Recent studies of the effects of neurotrophins (i.e., growth factors for nerves) have provided information that may be used to develop a gene therapy treatment for several retinal degenerations which would not require the identification of the mutation. For example, injection of bFGF or brain derived neurotrophic factor (BDNF) into the vitreous delays retinal degeneration and light-induced retinal degeneration in albino rats. LaVail et al., *Proc. Nat'l Acad. Sci. USA* 89:11249 (1992); Faktorovich et al., *Nature* 347:83 (1990). The effect, however, is transient and continued administration of the factor is required for long term preservation. If genes for these factors could be delivered to the eye, continued synthesis should be therapeutically useful.

Therefore, a need exists for a means to deliver therapeutic polypeptides or proteins on a continuous basis to treat neuronal degeneration.

SUMMARY OF THE INVENTION

In one aspect, the present invention provides methods for treating neuronal degeneration, including ocular neuronal degeneration, by administration of a recombinant Herpes simplex virus that stimulates expression of a therapeutic gene in infected cells.

The present invention also provides a replication competent Herpes simplex virus that expresses in infected cells a therapeutic gene and a functional product of the $_\gamma 34.5$ gene, but does not express functional ribonucleotide reductase.

DETAILED DESCRIPTION

1. Definitions

In the description that follows, a number of terms are utilized extensively. Definitions are herein provided to facilitate understanding of the invention.

Structural gene. A DNA sequence that is transcribed into messenger RNA (mRNA) which is then translated into a sequence of amino acids characteristic of a specific polypeptide (protein).

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Enhancer. A promoter element. An enhancer can increase the efficiency with which a particular gene is transcribed into MRNA irrespective of the distance or orientation of the enhancer relative to the start site of transcription.

Complementary DNA (cDNA). Complementary DNA is a single-stranded DNA molecule that is formed from an mRNA template by the enzyme reverse transcriptase.

Typically, a primer complementary to portions of MRNA is employed for the initiation of reverse transcription. Those skilled in the art also use the term "cDNA" to refer to a double-stranded DNA molecule derived from a single mRNA molecule.

Expression. Expression is the process by which a polypeptide is produced from a structural gene. The process involves transcription of the gene into mRNA and the translation of such mRNA into polypeptide(s).

Cloning vector. A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Recombinant host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989) ["Sambrook"].

RR⁻ or RR deficient HSV. A RR deficient, or "RR⁻," HSV is a Herpes simplex virus that does not produce functional ribonucleotide reductase.

Therapeutic gene. In the present context, a "therapeutic gene" is a gene that encodes a product used to treat a neuronal degenerative disease or disorder. Suitable therapeutic genes include growth factors, neurotrophins and cytokines.

2. Overview

Replication deficient viral vectors are frequently suggested for use in gene therapy because of safety concerns associated with using replication competent viruses. The problem with replication deficient viruses is that they infect one cell, and cannot propagate through a tissue or a larger area. Thus, if delivery is not efficient, only a limited number of cells are transformed. This is a serious limitation, particularly in the area of neural and ocular delivery, because replication is required for a virus to cross a synapse.

Replication deficient Herpes simplex viruses have been used as gene therapy vectors with the amplicon system. This system requires an amplicon (which contains the origin of replication and a packaging sequence from the virus, as well as the gene of interest), a helper cell line, and a helper cell virus. The cell line contains a gene which is essential for viral replication, so that when the helper cell line is infected with the helper virus, replication occurs. Some of the virus particles produced from this infection have packaged the amplicon, and some have packaged the helper cell virus, so it is then necessary to separate one from the other. A recent variation of this method uses a set of overlapping clones from the helper virus which has a deletion in the packaging sequence. This system results in packaging of only the amplicon. Previous attempts to deliver a gene to various parts of the eye have used adenoviruses, adeno-associated viruses, and Herpes simplex virus. So far, researchers have only been able to "label" retinal cells via subretinal injection, which causes retinal detachment in the area of the injection.

The mutant hrR3 vector has a deletion in the ribonucleotide reductase (RR) gene. The RR deficient virus replicates well in tissue culture, and to some extent in animals, but does not cause any significant pathology in animals. The inventors utilized a vector with the lacZ gene inserted into the area of the RR deletion, and used intravitreal injection, anterior chamber injection, and corneal scarification to introduce the vector into the eyes of mice and rats. After allowing sufficient time for gene expression, the animals were sacrificed, and examined for gene expression in the eye as evidenced by blue color. Corneal scarification resulted in gene expression in the area of scarification. When the vector was injected into the anterior chamber, the iris turned blue. Intravitreal injection resulted in columns of blue cells from the inner and outer nuclear layers to the ganglia. These columns provide evidence that the virus can cross synapses.

In addition, the inventors have inserted the gene for basic fibroblast growth factor (bFGF) into these vectors in the area of the ribonucleotide reductase deletion. Studies show that cells infected with the recombinant HSV vector express bFGF. This successful gene insertion was accomplished after three years of effort on the part of the inventors.

Initial attempts to create a viral vector incorporating a fibroblast growth factor gene in the area of the RR deletion were unsuccessful due to the natural limitations of creating such a vector. Such limitations include the fact that there must not be an overlapping gene present in the insertion that is essential. Furthermore, deletion of both the RR gene and a second "non-essential" gene may render the virus replication incompetent or so restricted in its growth that it cannot survive.

Initial constructs by the inventors attempted to insert the basic fibroblast growth factor (bFGF) gene into the latency-associated transcript (LAT) gene, which is expressed only in neurons. A HSV fragment encoding LAT and several kilobases of flanking DNA was cloned. The LAT gene was then cut just downstream of the LAT promoter, and the bFGF cDNA inserted to produce a plasmid, with the intention that the bFGF gene would then be controlled by the neuron specific LAT promoter. This plasmid was then transfected with purified hrR3 vector and attempts were made to plaque purify the LAT-bFGF recombinant. No simple screens to identify the recombinant existed, so plaques were chosen and their DNA analyzed by Southern blotting. Although a total of 500 plaques were screened, all results were negative. Although Southern blotting of the entire transfection mixture showed that bFGF gene had inserted into the hrR3 vector, no pure viral vectors containing the bFGF gene could be isolated. It was postulated that either the insertion of the bFGF gene disrupted some essential function of the virus, or more likely, that insertion of the bFGF gene resulted in a second disruption of the virus, that combined with the deletion in the RR gene, crippled viral growth to such an extent that a pure virus containing the bFGF gene insertion could not be isolated. Similar attempts utilizing a CMV-bFGF plasmid, as described in Example 2 infra, which was then inserted into the nonessential glycoprotein C gene and transfected with purified hrR3 DNA were unsuccessful. It was postulated that the combination of a glycoprotein C gene and RR gene deletion crippled viral growth in the manner previously described.

3. Construction of Replication Competent Herpes Simplex Virus Vectors That Express a Foreign Gene Various methods for gene therapy are available. These include placement of transfected cells carrying the gene into the host, delivery of naked DNA to muscle cells, use of cationic lipid carriers, and use of viruses such as retroviruses, adenoviruses, and Herpes simplex virus (HSV). See, for example, Meindl et al., *Nature Genetics* 13:35 (1996); Mulligan, *Science* 260:926 (1993); Rosenberg et al., *Science* 242:1575 (1988); LaSalle et al., *Science* 259:988 (1993); Wolff et al., *Science* 247:1465 (1990); Breakfield and Deluca, *The New Biologist* 3:203 (1991). HSV seems particularly suited for delivery of genes to neurons since infection of neurons is a normal part of the virus life cycle. Additional advantages of HSV-based vectors include the ability to deliver genes to non-dividing cells, and the ability to infect many cell types in both animals and humans. Fields (ed.), VIROLOGY, pages 527–561 (Raven Press 1985).

The inventors have identified genes in Herpes simplex virus-1 (HSV) that are involved in virulence. Brandt et al., *J. Gen. Virol.* 72:2043 (1991); Herold et al., *J. Gen. Virol.* 75:1211–1222 (1994); Visalli and Brandt, *Virology* 185:419 (1991). In particular, the HSV type 1 ribonucleotide reductase (RR) gene was found to be required for corneal virulence. Brandt et al., *J. Gen. Virol.* 72:2043 (1991). The RR gene was also found to be required for acute retinal disease. Brandt et al., *Arch. Virol.* 142:883 (1997).

In addition, Goldstein and Weller, *J. Virol.* 166:41 (1988), have shown that RR deficient mutants are severely compromised in the ability to replicate at 39.5° C. in vitro. Such mutants, therefore, are less likely to propagate in an infected host who has a fever. Furthermore, RR deficient HSV is hypersensitive to acyclovir and ganciclovir, and consequently, RR$^-$ HSV is responsive to antiviral therapy. Thus, RR deficient HSV have attenuated neurovirulence and are susceptible to antiviral therapy in the event that the host has viral encephalitis.

Martuza et al., U.S. Pat. No. 5,585,096 (1996), have described the production of replication competent HSV to kill tumor cells. Although the HSV vector is RR deficient, the vector also has a mutation in the $\gamma_1 34.5$ gene. As a result, the vector produces neither RR nor the product of the $\gamma_1 34.5$ gene. While the present invention contemplates an HSV vector having such a double mutation, the methods described herein do not require the use of such a vector. Suitable HSV vectors of the present invention are incapable of expressing the RR gene. Useful RR$^-$ vectors include those that express a functional product of the $\gamma_1 34.5$ gene, as well as vectors that are incapable of expressing a functional $\gamma_1 34.5$ gene product.

Those of skill in the art are capable of constructing HSV vectors that are RR deficient. See, for example, Goldstein and Weller, *J. Virol.* 62:196 (1988). HSV-1 DNA can be obtained, for example, from commercial sources such as the American Type Culture Collection (ATCC No. VR-260). HSV-2 DNA can be obtained, for example, from commercial sources such as The American Type Culture Collection (ATCC No. VR540).

A method for constructing a RR$^-$ vector that expresses a foreign gene is provided in Example 2 herein. In the example, a vector was produced that expresses a bovine bFGF gene under the control of the Human Cytomegalovirus Immediate Early gene promoter. Additional genes that are suitable for expressing in cell lines or for gene therapy include, but are not limited to, genes encoding: acidic fibroblast growth factor (aFGF; FGF-1); glial cell line-derived neurotrophic factor; brain-derived neurotrophic factor; ciliary neurotrophic factor; nerve growth factor; interleukin-1β; superoxide dismutase; extracellular matrix proteins (collagens, fibronectins, integrins); cell adhesion molecules; neurotransmitter receptors; ornithine amino transferase; prostaglandin synthesis regulation proteins; trabecular meshwork proteins; hypoxanthine phosphoribosyltransferase; tyrosine hydroxylase, and prostaglandin receptors.

Nucleotide sequences encoding these polypeptides are known to those of skill in the art. For example, Abraham et al., *Science* 233:545 (1986), disclose the nucleotide sequence of bovine bFGF, while the nucleotide sequence of human bFGF is disclosed by Abraham et al., *EMBO J.* 5:2523 (1986). Mergia et al., *Biochem. Biophys. Res. Commun.* 164:1121 (1989), provide the nucleotide sequence of the human aFGF gene. The nucleotide sequence of the rat glial cell line-derived neurotrophic factor is described by Springer et al., *Exp. Neurol.* 131:47 (1995). Maisonpeirre et al., *Genomics* 10:558 (1991), provide the nucleotide sequences of human and rat brain-derived neurotrophic factor, while Arab et al., *Gene* 185:95 (1997), disclose the amino acid sequence of bovine brain-derived neurotrophic factor. Rat ciliary neurotrophic factor is described by Stöcki et al., *Nature* 342:920 (1989). The nucleotide sequence of the human ciliary neurotrophic factor gene is disclosed by Negro et al., *Eur. J. Biochem.* 201:289 (1991), Lin et al., *Science* 246:1023 (1989), and by Lam et al., *Gene* 102:271 (1991). Ulrich et al., *Nature* 303:821 (1983), provide a comparison of human and murine coding regions of beta-nerve growth factor genes. The nucleotide sequence of bovine interleukin-β1 is disclosed by Leong et al., *Nucl. Acids Res.* 16:9054 (1988), while Bensi et al., *Gene* 52:95 (1987), provide the nucleotide sequence of the human interleukin-1β gene.

DNA molecules encoding such polypeptides can be obtained by screening cDNA or genomic libraries with polynucleotide probes having nucleotide sequences based upon known genes. Standard methods are well-known to those of skill in the art. See, for example, Ausubel et al. (eds.), SHORT PROTOCOLS IN MOLECULAR BIOLOGY, 3rd Edition, pages 2-1 to 2-13 and 5-1 to 5-6 (John Wiley & Sons, Inc. 1995).

Alternatively, DNA molecules encoding growth factors can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990). Also, see Wosnick et al., *Gene* 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize DNA molecules at least two kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263–268, (Humana Press, Inc. 1993); Holowachuk et al., *PCR Methods Appl.* 4:299 (1995).

DNA molecules encoding growth factors can also be obtained from commercial sources. For example, a clone of the human aFGF gene can be obtained from the American Type Culture Collection (ATCC No. 53335).

High titer stocks of recombinant HSV can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211–1222 (1994), Visalli and Brandt, *Virology* 185:419 (1991), Grau et al., *Invest. Ophthalmol. Vis. Sci.* 30:2474 (1989), and by Brandt et al., *J. Virol. Meth.* 36:209 (1992). Also see, Brown and MacLean (eds.), HERPES SIMPLEX VIRUS PROTOCOLS (Humana Press 1997).

4. Use of RR Deficient HSV to Produce Proteins in Cell Lines

To express the foreign polypeptide, the DNA sequence encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

Foreign proteins of the present invention are preferably expressed in mammalian cells. Examples of mammalian host cells include African green monkey kidney cells (Vero; ATCC CRL 1587), human embryonic kidney cells (293-HEK; ATCC CRL 1573), baby hamster kidney cells (BHK21; ATCC CRL 8544), canine kidney cells (MDCK; ATCC CCL 34), Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene [Hamer et al., *J. Molec. Appl. Genet.* 1:273 (1982)], the TK promoter of Herpes virus [McKnight, *Cell* 31:355 (1982)], the SV40 early promoter [Benoist et al., *Nature* 290:304 (1981)], the Rous sarcoma virus promoter [Gorman et al., *Proc. Nat'l Acad. Sci. USA* 79:6777 (1982)], the cytomegalovirus promoter [Foecking et al., *Gene* 45:101 (1980)], and the mouse mammary tumor virus promoter. See, generally, Etcheverry, "Expression of Engineered Proteins in Mammalian Cell Culture," in PROTEIN ENGINEERING: PRINCIPLES AND PRACTICE, Cleland et al. (eds.), pages 163–181 (John Wiley & Sons, Inc. 1996).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10:4529 (1990); Kaufman et al., *Nucl. Acids Res.* 19:4485 (1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), GENE TRANSFER AND EXPRESSION PROTOCOLS (Humana Press 1991).

General methods for expressing and recovering foreign protein produced by a mammalian cell system is provided by, for example, Etcheverry, "Expression of Engineered Proteins in Mammalian Cell Culture," in PROTEIN ENGINEERING: PRINCIPLES AND PRACTICE, (Cleland et al., eds.), pages 163–181 (Wiley-Liss, Inc. 1996).

5. Use of RR Deficient HSV to Treat Ocular and Neural Diseases

As briefly discussed above, various polypeptides are useful for treatment of ocular and neural diseases. For example, subretinal or intravitreal injection of a number of growth factors, cytokines and neurotrophins (bFGF, brain derived growth factor, interleukin-1β) have been shown to restore specific functions to retinal or retinal pigment epithelial cells and to retard photoreceptor cell death in various animal models of retinal degeneration. Faktorovich et al., *Nature* 347:83 (1990); LaVail et al., *Proc. Nat'l Acad. Sci. USA* 89:11249 (1992). Moreover, Faktorovich et al., *Nature* 347:83 (1990), have shown that the rate of photoreceptor degeneration can be significantly slowed by an intraocular injection of bFGF in Royal College of Surgeons rats that have inherited retinal dystrophy. Intraocular administration of bFGF also protects photoreceptors from light-induced degeneration in albino rats, a noninherited form of retinal degeneration. LaVail et al., *Ann. N.Y. Acad. Sci.* 638:341 (1991).

Similarly, Unoki and LaVail, *Invest. Ophthalmol. Vis. Sci.* 35:907 (1994), showed that intravitreal injection of brain-derived neurotrophic factor, ciliary neurotrophic factor and basic FGF at least transiently protects rat retina from ischemic injury. Also see, Zhang et al., *Invest. Ophthalmol. Vis. Sci.* 35:3163 (1994). Furthermore, implants with either basic FGF or acidic FGF can rescue adult retinal ganglion cells from axotomy-induced cell death in rats. Sievers et al., *Neurosci. Lett.* 76:157 (1987). Also see, GROWTH FACTORS AS DRUGS FOR NEUROLOGICAL AND SENSORY DISORDERS—SYMPOSIUM NO. 196, CIBA Foundation Symposia Series (1996).

Accordingly, recombinant HSV vectors that express growth factors, cytokines and neurotrophins are suitable for treating ocular neuronal degenerative diseases and disorders, including retinitis pigmentosa, macular degeneration, glaucoma, optic neuropathies, and trauma. The recombinant vectors described herein are also suitable for treating diseases and disorders involving neuronal degeneration. Such diseases include Alzheimer's Disease, stroke, trauma, and retinal degeneration.

The efficacy of any particular HSV vector that expresses a therapeutic protein can be tested in an appropriate animal model of a neuronal degenerative disease or disorder. As an illustration, see Example 5.

In general, it is desirable to administer the highest dose possible without inducing toxicity. The actual dose will vary depending on the volume of vector preparation that can be introduced and this varies depending on the site of administration. The titer of stocks can be as high as $1\times10^9$–$1\times10^{10}$ Plaque Forming Units (PFU)/ml. In the human eye it should be possible to give at least 100 µl per injection, which is equivalent to $1\times10^8$–$1\times10^9$ PFU per injection. In the brain, this volume should also be possible. Peripheral or intravenous injection could deliver a much higher dose. Multiple administration may also make it possible to increase the dose.

Administration of recombinant HSV to a patient can be via injection, including intravenous and intravitreal injection, and by infusion into the cerebrospinal fluid, or by other means well known in the art.

A composition comprising recombinant Herpes simplex viruses of the present invention can be formulated according to known methods to prepare pharmaceutically useful compositions, whereby viruses are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (Mack Publishing Co. 1995), and GILMAN'S THE PHARMACOLOGICAL BASIS OF THERAPEUTICS, 7th Ed. (MacMillan Publishing Co. 1985).

For purposes of therapy, a recombinant Herpes simplex virus and a pharmaceutically acceptable carrier are administered to a subject in a therapeutically effective amount. A combination of virus and a pharmaceutically acceptable carrier is said to be administered in a "therapeutically effective amount" if the amount administered is physiologically significant. An agent is physiologically significant if its presence results in a detectable change in the physiology of a recipient subject. In the present context, an agent is physiologically significant if its presence inhibits the progress of neuronal degeneration.

The present invention, thus generally described, will be understood more readily by reference to the following examples, which are provided by way of illustration and are not intended to be limiting of the present invention.

EXAMPLE 1

Distribution of the RR⁻ Vector Virus (hrR3) in Rat Tissues

To determine the cell types that are infected with an HSV vector, rats were exposed to hrR3, an RR deficient mutant virus. Construction of the hrR3 vector is described by Goldstein and Weller, *J. Virol.* 62:196 (1988). The hrR3 virus has the *E. coli* lacZ gene inserted into the RR locus. The expression of the lacZ gene results in the formation of blue colored plaques in the presence of X-gal substrate.

In these studies, rats were injected with hrR3 virus, and seven days later, tissues were collected for analysis. The tissues injected included the visual cortex, vitreous, anterior chamber, and cornea. Analysis of six treated rat brains revealed X-gal staining at the site of the injections (i.e., primary visual cortex) and in the lateral geniculate nucleus (LGN). This result shows that a foreign gene can be delivered and expressed using this vector, and that the vector can spread to neurons quite distant from the infection site. Uptake was specific since lacZ staining was only seen in the visual cortex and LGN. Other sites had blue cells, but this was due to endogenous lacZ expression as determined from control brains of rats that had not received the virus. As determined by morphology, up to about 300 neurons were labeled in each positive LGN. When $1\times10^6$–$1\times10^7$ PFU were injected intraviterally, lacZ staining was seen in the retinal pigment epithelium, non-pigmented ciliary body epithelium, photoreceptor cells, and cells in the inner nuclear layer. Cells in the optic nerve were also labeled on occasion. Injection of $1\times10^6$–$1\times10^7$ PFU into the anterior chamber resulted in labeling in the iris and the angle of the eye (trabecular meshwork cells). Uninjected eyes or PBS injected eyes are negative for lacZ staining. After corneal scarification, only cells along the corneal scratches are labeled.

EXAMPLE 2

Delivery of BFGF to Sites of Neuronal Damage Using Transfected Cells

A study was performed to test the possibility that the efficacy of basic fibroblast growth factor (bFGF) treatment could be improved by prolonging the exposure of axotomized lateral geniculate nucleus (LGN) neurons to bFGF. Briefly, quail teratocarcinoma cells (QT6) were obtained from American Type Culture Collection (ATCC, Baltimore, Md.), and grown in M199 media (Gibco BRL; Bethesda, Md.) containing 10% tryptose phosphate broth, 2.5 units/ml penicillin, 2.5 µg/ml streptomycin (Gibco BRL), 1% DMSO and 5% fetal calf serum (Hyclone, Logan, Utah). To produce the bFGF-positive (QBF) cells, a 616 base pair BamHI and EcoRV fragment containing the wild type CDNA for the bovine bFGF gene was cleaved from the plasmid pBSbFGF and inserted into the multiple cloning region of the plasmid pCDNA3 (Invitrogen, CA). The nucleotide sequence of the bFGF gene is disclosed by Abrahams et al., *Science* 233:545 (1986).

The expression of the bovine bFGF gene was driven by the human cytomegalovirus immediate early enhancer-promoter (CMV). This plasmid also included the neomycin resistance gene, allowing for selection in eukaryotic cells using G418. QT6 cells were transfected with pCDNA3-bFGF using a low $CO_2$, low pH, modified calcium phosphate precipitation protocol. See, for example, Chen and Okayama, *Mol. Cell. Biol.* 7:2745 (1987). Two days later, transfected QBF cells and control QT6 cells were replated at identical densities and placed in medium containing 600 µg/ml G418. Cells were passaged every three days until all the control cells were dead (approximately three weeks). Stably transfected QBF cells were then maintained in medium containing 300 µg/ml G418.

Stable incorporation of the bovine bFGF gene into the transfected quail cells was demonstrated by Southern Blot analyses using a 616 base pair EcoRI fragment which included the entire bovine bFGF cDNA as a probe. To determine whether the CMV-bFGF construct was transcribed in the QBF cells, total cellular RNA from QBF and QT6 cells was analyzed by Northern blotting analysis, using the bFGF cDNA as a probe. A transcript of the predicted size (~800 base pairs) was readily detected in the RNA from QBF cells, but not in RNA from the QT6 cells. The ability of the QBF cells to make bFGF protein was determined by Western blot analysis. When probed with an anti-bovine bFGF antibody, three bands of 18 KD, ~22 KD and ~16 KD were seen in the QBF cell lane, compared to a single 18 KD band seen in this range in the QT6 cell lane. Based on the amount of protein present in the control lanes, it was estimated that the QBF cells made approximately 0.14–1.4 fg of bFGF protein per cell. Moreover, the expression of the bovine bFGF gene appeared to give a mitogenic advantage to the transfected cells, suggesting that functional bFGF protein was being made by the QBF cells.

Rats having a lesion of the visual cortex received implants of quail cells transfected with the bFGF gene, and were compared with rats that received either a single administration of bFGF protein directly, 0.9% saline, or untransfected quail cells. Rats were sacrificed at one, two, or four weeks after the cortical lesion was made, and the total number of surviving lateral geniculate nucleus neurons and their mean cross-sectional areas were determined.

The results of these experiments showed that, at one week postoperatively, the numbers of surviving LGN neurons in QBF cell implanted rats were 136% greater than in saline-treated control rats. However, at two and four weeks, neuronal numbers in QBF cell implanted rats were similar to saline-treated controls.

In contrast to the transient neuroprotective effects on neuronal cell numbers, the effects on mean neuronal cross-sectional areas were long-term, lasting up to four weeks. These surviving neurons exhibited mean areas that were consistently larger than the controls (19%, 48% and 35% larger at one, two and four weeks). Surprisingly, the neuroprotective effects of the QBF cell implants were different from those seen after a single administration of the recombinant human bFGF protein alone, which prevented neuronal loss for at least three months, but did not reduce cell atrophy. Accordingly, quail teratocarcinoma cells transfected with the bovine bFGF gene and implanted at the site of a visual cortex lesion are capable of reducing both neuronal death and atrophy of axotomized LGN neurons.

EXAMPLE 3

Insertion of the bFGF Gene Into the Ribonucleotide Reductase Locus

As discussed supra, prior attempts to insert the bFGF gene into the LAT and gC locus of HSV DNA failed. The reasons are not clear, but may be due to the deletion of two genes in the virus (RR and LAT, or RR and gC).

An attempt was then made to insert the bFGF gene into the RR locus to produce a virus with only a single gene disruption. To accomplish this, the CMV-bFGF gene was transferred to a plasmid, pMAK. The pMAK plasmid contains the HSV-1 RR gene interrupted by the *E. coli* lacZ gene. The CMV-bFGF gene was inserted into the middle of the lacZ coding region. The resulting plasmid, "PMAK bFGF" thus carried the CMV-bFGF gene flanked by lacZ sequences which are then flanked by HSV-1 RR sequences.

The CMV-bFGF gene was inserted into the lacZ gene of the hrR3 virus. Recombinants were identified by selecting for colorless plaques. The pMAK-bFGF sequences were inserted into hrR3 by co-transfecting purified hrR3 DNA with pMAK bFGF into African green monkey kidney (Vero) cells. The resulting virus pool was then plaqued on Vero cell monolayers in the presence of X-gal and infected cells were screened for colorless plaques. A total of 14 such plaques were picked and replaqued two more times. Thus, each of the 14 plaques were purified three times and the stock viral preparations were completely free of blue plaque virus (wild type hrR3).

In order to identify viruses carrying the bFGF gene, viral DNA was purified, digested with EcoRI or EcoRV, and analyzed using Southern blot analysis with bFGF probe. Since EcoRI releases the bFGF sequence, a 600 base pair EcoRI fragment should be identified on the blots. EcoRV cleaves once in PMAK bFGF so this digest should contain a bFGF containing fragment that extends into the flanking viral DNA confirming the gene was integrated into the hrR3 genome. Of the 14 plaques, two gave the predicted fragment patterns. These two viruses were designated HSV-2526 and HSV-5042. The presence of the bFGF gene in the viruses was confirmed by re-isolating DNA and repeating the Southern analysis. Moreover, analysis of RNA from cells infected with either HSV-2526 or HSV-5042 demonstrated the production of bFGF RNA transcripts. In addition, immunoblot analysis showed that HSV-2526- and HSV-5042-infected cells produce bFGF protein.

EXAMPLE 4

Localization of BFGF Gene Expression in Animals Infected With RR Deficient HSV

To identify the distribution of bFGF expression, rats are injected with the bFGF-virus and at 1, 3, 5, and 7 days post-injection, the eyes are collected and processed for histology and immunohistochemical localization of bFGF antigens. Brandt et al., *Curr. Eye Res.* 13:755 (1994). For histology, eyes are fixed in phosphate buffered saline containing 10% formalin for three hours. The tissues are then embedded in paraffin, sectioned, and stained with hematoxylin/eosin by standard methods. Brandt et al., *Curr. Eye Res.* 13:755 (1994). For immunohistochemistry, eyes are embedded in OCT compound, snap frozen and sectioned with a cryomicrotome. They are then stained for bFGF using commercially available anti-bovine bFGF antisera (Dako, Carpinteria, Calif.) followed by alkaline phosphatase conjugated secondary antibody (Sigma, St. Louis, Mo.). Appropriate controls, such as non-specific antisera and secondary antibody only, are included, as are uninfected eyes.

The measurement of bFGF expression presents a problem in distinguishing between synthesis from the endogenous host gene and synthesis from the CMV-bFGF gene. Although increased bFGF protein may be detected levels in infected cells by immunohistochemistry as described above, available antibodies do cross react with rodent and bovine bFGF.

The use of reverse transcription-polymerase chain reaction (RT-PCR) provides reliable detection of CMV-bFGF gene expression. To make the assay specific for the delivered gene, 5' primers are used that anneal to sequences in the CMV promoter between the TATAA box and the bFGF coding region. The 3' primer anneals in the coding region of the bovine bFGF gene. β-Actin is amplified as a control. This method corrects for the differences in the size of the tissue sample used for analysis, as described previously. Brandt et al., *Curr. Eye Res.* 13:755 (1994).

Retina and ciliary body/iris are examined for bFGF RNA. Tissues are sampled at various times (days 3 or 4, 1 week, 2 weeks, 1 month, and 2 months). If the expression of the CMV-bFGF gene decreases to low levels before 1–2 months, the bFGF virus is re-administered. Expression and the effect on retinal degeneration are monitored. A total of 3–5 rats are analyzed at each time point.

EXAMPLE 5

Analysis of HSV Expressing Brain-Derived Neurotropic Factor in Animal Model Systems Vectors expressing brain-derived neurotrophic factor (BDNF) can be tested in in vivo models of retinal degeneration, which are available in both rats and mice. An advantage of the light-induced degeneration in the albino rat model is that one can control the onset of degeneration. LaVail et al., *Proc. Nat'l Acad. Sci. USA* 89:11249 (1992). In this way, it is possible to be precise about when treatment and onset of disease begin.

Rats are obtained from a commercial source, such as Harlan Sprague Dawley (Indianapolis, Ind.), and are maintained on standard food and water ad libitum as well as on a 12 hr:12 hr (light-dark) cycle at less than 2.0 footcandle illuminance. Retinal degeneration is induced by increasing the light levels to 115 to 200 footcandles, and maintaining continuous light exposure, as described previously. LaVail et al., *Proc. Nat'l Acad. Sci. USA* 89:11249 (1992).

For treatment, rats are anesthetized with intramuscular ketamine (84 mg/kg) and intraperitoneal xylazine (12 mg/kg). The viruses are delivered by intravitreal injection by inserting a 32 ga. needle in the right eye through the sclera into the vitreous just posterior to the corneal scleral junction on the nasotemporal side. A 5 $\mu$l suspension of virus ($1.0 \times 10^7$ to $1.0 \times 10^8$ pfu/ml) is injected using a Hamilton syringe. The needle is left in the eye for 60 seconds to equilibrate pressure, and then removed. The rats are monitored until recovery and then returned to animal care.

In initial studies, rats are sacrificed at 7 and 14 days for evaluation. If these early points suggest a positive effect, studies can be extended to months to evaluate long term effects. Typically, there will be three groups: hrR3 control, media control, and the HSV-2526 or HSV-5042 virus. An additional control is provided by the contralateral (left) eye, because an RR mutant virus does not cross into the contralateral eye. Additional rats are sacrificed at various times to test for the presence of virus and expression of the bFGF gene. At minimum, rats are examined at days 4, 7, 14, one month, and two months. If these initial studies are positive, the studies will be extended to longer times.

Rats are killed by $CO_2$ inhalation and then perfused intravascularly with phosphate buffered saline containing 2% paraformaldehyde and 2.5% glutaraldehyde. The eyes are bisected along the vertical meridian, embedded in epoxy resin, sectioned (1 $\mu$m thick) and stained with toluidine blue. Sections are cut along the vertical meridian and contain all of the retina extending from the ora serrata in the inferior hemisphere passing through the optic nerve head. To insure that oblique sections are not analyzed, the alignment of the rod outer segments are examined to confirm that they lie in the plane of the section. Slightly oblique sections show tangential fragments of the outer segments and are not used.

Previous studies have shown that changes in retinal cell number (degeneration) result in thinning of the affected cell layer. LaVail et al., *Proc. Nat'l Acad. Sci. USA* 89:11249 (1992); Michon et al., *Invest. Ophthalmol. Vis. Sci.* 32:280 (1991); Unoki and LaVail, *Invest. Ophthalmol. Vis. Sci.* 35:907 (1994); Zhang et al., *Invest. Ophthalmol. Vis. Sci.* 35:3163 (1994); Olsson et al., *Neuron* 815–830 (1992). Retinal degeneration will be quantified by measuring the mean thickness of (1) retina from the outer limiting membrane to the inner limiting membrane, (2) the border of the inner plexiform layer to the inner limiting membrane, (3) the inner nuclear layer, and (4) the outer nuclear layer. These are essentially the methods used by Unoki and LaVail, *Invest. Ophthalmol. Vis. Sci.* 35:907 (1994), and Zhang et al., *Invest. Ophthalmol. Vis. Sci.* 35:3163 (1994). If necessary, eye tissues may also be examined by transmission electron microscopy to detail cell structure and preservation, as described previously. Brandt et al., *J. Invert. Pathol.* 32:12 (1978).

In a similar manner, studies can be extended to other animal models of disease to determine if the treatment will be broadly applicable. Suitable models include the Royal College of Surgeons Rat, the rd mouse, and the rds mouse.

All references discussed supra are hereby incorporated by reference.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method of administering a Herpes simplex virus (HSV) for treating a subject having retinal degeneration, comprising the step of:

(a) administering to the eye of the subject a replication competent avirulent HSV that expresses a growth factor gene in the cells of the subject that are infected with the HSV;

wherein following administration of the HSV, the growth factor gene is delivered via the HSV into a target cell within the subject and the growth factor gene is expressed in an effective amount and for a sufficient duration within the target cell of the subject to have a therapeutic effect upon retinal degeneration, and wherein the HSV does not stimulate the expression of functional viral ribonucleotide reductase in the infected cells.

2. The method of claim 1, wherein the growth factor is selected from the group consisting of acidic fibroblast growth factor, basic fibroblast growth factor, and nerve growth factor.

3. The method of claim 2, wherein the growth factor is basic fibroblast growth factor.

4. The method of claim 1, wherein the genome of the HSV comprises a promoter that is operatively linked to the growth factor gene.

5. The method of claim 4, wherein the promoter is the Human Cytomegalovirus Immediate Early gene promoter.

6. The method of claim 5, wherein the growth factor gene encodes basic fibroblast growth factor.

7. A replication competent Herpes simplex virus (HSV) comprising a therapeutic gene, wherein said HSV expresses in cells infected with the HSV a therapeutic gene that is selected from the group consisting of a growth factor, a neurotrophin, and a cytokine, wherein the HSV also expresses a functional product of the $_\gamma 34.5$ gene, but does not express functional ribonucleotide reductase, and further wherein the therapeutic gene is inserted in the ribonucleotide reductase gene locus of the HSV.

8. A method of delivering and expressing a foreign gene to a target cell within a primate eye, comprising the step of:

(a) administering to the eye of the primate subject a replication competent avirulent simplex virus HSV;

wherein following administration of the HSV, the foreign gene is delivered via the HSV into the target cell of the eye of the primate subject and the foreign gene is expressed at a detectable level within the target cell, and wherein the HSV does not stimulate the expression of functional viral ribonucleotide reductase in the infected cell.

9. The method of claim 8, wherein the genome of the HSV comprises a promoter that is operatively linked to the foreign gene.

10. The method of claim 9, wherein the promoter is the human cytomegalovirus immediate early gene promoter.

* * * * *